United States Patent [19]

Ichijima et al.

[11] 4,133,686

[45] Jan. 9, 1979

[54] COLOR PHOTOGRAPHIC LIGHT-SENSITIVE ELEMENT

[75] Inventors: Seiji Ichijima; Nobuo Furutachi, both of Minami-ashigara, Japan

[73] Assignee: Fuji Photo Film Co., Ltd., Minami-ashigara, Japan

[21] Appl. No.: 846,071

[22] Filed: Oct. 27, 1977

[30] Foreign Application Priority Data

Oct. 29, 1976 [JP] Japan .................................. 51-130770

[51] Int. Cl.$^2$ ................................................ G03C 1/40
[52] U.S. Cl. ............................................ 96/74; 96/56; 96/95; 96/100 R
[58] Field of Search ................... 96/100, 56.5, 56, 95, 96/74

[56] References Cited

U.S. PATENT DOCUMENTS

| 2,311,082 | 2/1943 | Porter et al. .......................... 96/56.5 |
| 3,623,871 | 11/1971 | Van Poucke et al. ................ 96/56.5 |
| 3,935,015 | 1/1976 | Arai et al. ............................. 96/100 |
| 3,960,571 | 6/1976 | Okumura et al. ..................... 96/100 |
| 4,015,988 | 4/1977 | Shiba et al. ............................ 96/56 |

*Primary Examiner*—J. Travis Brown
*Attorney, Agent, or Firm*—Sughrue, Rothwell, Mion, Zinn and Macpeak

[57] ABSTRACT

A color photographic light-sensitive element comprising a support having thereon a silver halide emulsion layer containing therein a 3-anilino-2-pyrazolin-5-one magenta color forming coupler, which prevents yellow staining at the unexposed areas after color development processing, and which particularly prevents an increase in yellow staining due to irradiation of light with the magenta color images obtained using the color photographic element containing the magenta coupler maintaining a clear color even after irradiation of light.

4 Claims, No Drawings

COLOR PHOTOGRAPHIC LIGHT-SENSITIVE ELEMENT

BACKGROUND OF THE INVENTION

1. Field of the Invention

The present invention relates to a silver halide photographic light-sensitive element containing a magenta color forming coupler.

2. Description of the Prior Art

After exposing a silver halide photographic light-sensitive element to light, the element is developed with an aromatic primary amino developing agent. The developing agent is ozidized by color development and reacts with a coupler to form a dye, thus, a color image being formed. In this system, a subtractive method is generally used for color reproduction, in which blue, green and red colors are reproduced by forming yellow, magneta and cyan color images which are in complimentary relation thereto, respectively. In general, acylacetamide or dibenzoylmethane type couplers are employed for forming yellow color images, pyrazolone, cyanoacetyl or indazolone type couplers are used for forming magenta color images, and phenol type couplers, for example, phenols and naphthols, are utilized for forming cyan color images.

To produce color photographs, couplers which form dyes are incorporated into a developer or are present in a light-sensitive photographic emulsion layer(s). p A variety of 5-pyrazolone type couplers for forming magenta color images are known. Known substituents at the 3-position of the 5-pyrazolone ring include an alkyl group, an aryl group, the alkoxy groups as described in U.S. Pat. No. 2,439,098, the acylamino groups as described in U.S. Pat. Nos. 2,369,489 and 2,600,788, and the ureido groups as described in U.S. Pat. No. 3,558,319 and an anilino group. 3-Anilino-5-pyrazolone type couplers have often been described in the art since U.S. Pat. No. 2,311,081 (U.S. Reissue Pat. No. 22,329) was issued and several improvements have been proposed. British Patent No. 956,261 discloses that azomethine dyes obtained from derivatives in which the ortho position of the anilino group is substituted with an alkoxy group or a halogen atom have advantageous spectral absorption for color photography in that undesired absorption in the red light region is particularly low.

Specific examples of diffusion resistant couplers which belong to this type and are capable of being incorporated into photographic emulsions are described in U.S. Pat. Nos. 3,930,861, 3,907,571, 3,928,044 and 3,935,015, etc. For example, the couplers described in U.S. Pat. No. 3,935,015 are well known and are 3-(acylaminoanilino)-5-pyrazolones represented by the formula (M) below:

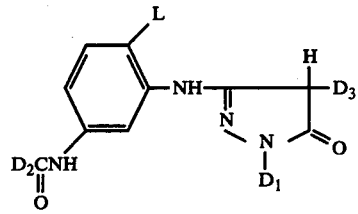

(M)

wherein $D_1$ represents an aryl group or a heterocyclic group, $D_2$ represents a straight chain, branched chain or cyclic alkyl group having 7 to 23 carbon atoms, $D_3$ represents a splitting off group, and L represents an alkoxy group having 1 to 18 carbon atoms or a halogen atom.

These couplers have the characteristics that the undesired absorption of magenta azomethine dyes obtained upon color formation using the same in the red light region is low, the cut off of the main absorption is good at the longer wavelength side, and magenta color images having a high color density are obtained because the coloration speed is high, and, further, the solubility in organic solvents having a high boiling point is improved so that, after dissolving these couplers in organic solvents, the couplers are emulsion dispersed in an aqueous medium in the form of colloidal particles and then added to emulsions. However, these couplers have the disadvantages that the degree of yellow staining at the unexposed portion after color development processing is high and this degree of yellow staining is increased upon irradiation with light, and, further, have the disadvantages that color fading of the magenta color images obtained upon color development using the same occurs to a marked degree upon irradiation with light and the color balance required for color photography is damaged by exposure to light. These disadvantages become fatal defects for color light-sensitive elements such as color printing papers and the like. Thus, improved couplers which do not have these disadvantages have been strongly desired.

SUMMARY OF THE INVENTION

A first object of the present invention is to provide a coupler which minimizes the formation of yellow stain at the unexposed areas of a color photographic light-sensitive element after color development processing, and, further, which does not increase the yellow stain nor cause a fresh yellow stain upon irradiation with light.

A second object of the present invention is to provide a coupler having the property that color images formed therefrom fade with difficulty even if the magenta color images obtained after color development are irradiated with light.

A third object of the present invention is to provide a light-sensitive element which can be used to reproduce a clear color by the subtractive method.

A fourth object of the present invention is to provide a light-sensitive element which is suitable for a simple development processing without stabilizing processing with formaldehyde or the like being required.

A fifth object of the present invention is to provide a coupler which has a high color formation rate and provides magenta color images having a high density.

A sixth object of the present invention is to provide a coupler which has excellent solubility in an organic solvent and is suitable for use in the oil solution method which comprises emulsion dispersing the coupler in an aqueous medium in the form of fine colloidal particles and then incorporating the dispersion into an emulsion.

A seventh object of the present invention is to provide a method for producing a light-sensitive element using a magenta color image forming coupler which can be relatively easily synthesized using a starting material which is easy to obtain.

These and other objects of the present invention will become more apparent from the detailed description of the invention and the examples hereinbelow.

These objects can be effectively achieved by incorporating into a silver halide photographic emulsion layer(s) of a color photographic light-sensitive element, as a magenta color image forming coupler, a 3-anilino-5-pyrazolone coupler wherein the anilino group thereof is substituted with a halogen atom at the 2-position of the anilino group and with a halogen atom or at the 4-position of the anilino group, and further with the anilino group having an alkoxy group, an aryloxy group or a heterocyclic oxy group at the 5-position of the anilino group. It is preferred for the 1-position of the pyrazolone ring to be substituted with a 2,4,6-trichlorophenyl group. Further, the 4-position of the pyrazolone nucleus may also be a hydrogen atom, or may be substituted with a coupling off group.

DETAILED DESCRIPTION OF THE INVENTION

The term "coupling off group" as used herein has the same meaning generally used in the color-forming coupler field and refers to a group which is eliminated by the oxidation product of an aromatic primary amino developing agent.

Couplers which are useful for the present invention include compounds represented by the following general formula (I):

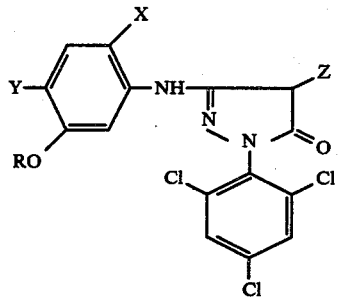

wherein R represents an aliphatic hydrocarbon group having up to about 35 carbon atoms (including substituted groups, examples of which are an alkyl group, an alkenyl group, a cycloalkyl group, a cycloalkenyl group, an aralkyl group, etc.), a heterocyclic group (the cyclic groups referred to above can contain, for example, 5- or 6-membered rings), or an aromatic hydrocarbon group (e.g., an aryl group); X represents a halogen atom; Y represents a halogen atom; and Z represents a hydrogen atom or a coupling-off group.

R, X, Y and Z in the general formula (I) above are described in detail hereinbelow.

In the general formula (I), R can be a straight chain or branched chain group and preferably represents a straight chain or branched chain alkyl group (e.g., a methyl, ethyl, heptyl, tetradecyl, hexadecyl, octadecyl, dodecyl, etc. group), a straight chain or branched chain alkenyl group (e.g., an allyl, etc. group), a cycloalkyl group (including a bridged cyclic hydrocarbon group, e.g., a cyclopentyl, cyclohexyl, norbornyl, etc. group), an aralkyl group (e.g., a benzyl, phenethyl, etc. group), a cycloalkenyl group (e.g., a cyclopentenyl, cyclohexenyl, etc. group), having 1 to 22 carbon atoms; which can be substituted with one or more substituents selected from halogen, nitro, cyano, aryl (e.g., phenyl, naphthyl, etc.), alkoxy (e.g., methoxy, ethoxy, etc.), aryloxy (e.g., phenyloxy, naphthyloxy, etc.), carboxy, alkylcarbonyl (e.g., acetyl, tetradecanoyl, etc.), arylcarbonyl (e.g., benzoyl, etc.) alkoxycarbonyl (e.g., methoxycarbonyl, benzyloxycarbonyl, etc.), aryloxycarbonyl (e.g., phenyloxycarbonyl, p-tolyloxycarbonyl, etc.), sulfo, acyloxy (e.g., acetyloxy, tetradecanoyloxy, etc.), sulfamoyl (e.g., N-ethylsulfamoyl, N-octadecylsulfamoyl, etc.), carbamoyl (e.g., N-ethylcarbamoyl, N-methyl-N-dodecylcarbamoyl, etc.), acylamino (e.g., acetylamino, benzamido, etc.), diacylamino (e.g., succinimido, hydantoinyl, etc.), ureido (e.g., methylureido, phenylureido, etc.), thioureido (e.g., phenylthioureido, etc.), urethane (e.g., tetradecyloxycarbonylamino, phenoxycarbonylamino, etc.), thiourethane (e.g., methoxythiocarbonylamino, etc.), sulfonamido (e.g., methanesulfonamido, etc.), heterocyclic (e.g., furyl, pyridyl, thienyl, etc.), arylsulfonyloxy (e.g., phenylsulfonyloxy, etc.), alkylsulfonyloxy (e.g., methanesulfonyloxy, dodecylsulfonyloxy, etc.), arylsulfonyl (e.g., phenylsulfonyl, etc.), alkylsulfonyl (e.g., methylsulfonyl, butylsulfonyl, etc.), alkylsulfinyl (e.g., methylsulfinyl, octadecylsulfinyl, etc.), arylsulfinyl (e.g., phenylsulfinyl, etc.), alkylamino (e.g., methylamino, dodecylamino, etc.), dialkylamino (e.g., N,N-diethylamino, N-methyl-N-dodecylamino, etc.), anilino (e.g., phenylamino, p-methoxyphenylamino, etc.), N-arylanilino (e.g., N-phenylanilino, N-phenyl-N-(4-methoxyphenyl)amino, etc.), N-alkylanilino (e.g., N-methylanilino, N-butylanilino, etc.), N-acylanilino (e.g., N-acetylanilino, N-trichloroacetylanilino, etc.), hydroxy and mercapto. Where R is an alkyl group substituted with a fluorine atom, R can also be a perfluoroalkyl group. Further, R represents a monocyclic or bicyclic aromatic group, e.g., an aryl group (for example, a phenyl, α- or β-naphthyl, etc. group) and an aryl group having at least one substituent. Suitable substituents can be an aliphatic hydrocarbon group, as described above, an arylthio group (for example, a phenylthio, naphthylthio, etc. group) or an alkylthio group (for example, a methylthio, ethylthio, etc. group).

Furthermore, R represents a heterocyclic group (for example, a 5- or 6-membered heterocyclic ring or condensed heterocyclic ring group containing, as a hetero atom, a nitrogen atom, an oxygen atom and/or a sulfur atom; e.g., a pyridyl, quinolyl, furyl, benzothiazolyl, oxazolyl, imidazolyl, naphthoxazolyl, etc. group) or a heterocyclic group which is substituted with one or more of the substituents as described above for the aryl group.

In the general formula (I), Z represents a hydrogen atom and, in addition thereto, a coupling-off group. Suitable coupling-off groups represented by Z are, for instance, a thiocyano group, an acyloxy group (e.g., an acetoxy, dodecanoyloxy, octadecanoyloxy, 3-pentadecylphenoxyacetoxy, benzoyloxy, β-naphthoyloxy, 3-[γ-(2,4-di-tert-amylphenoxy)butyramido]benzoyloxy, etc. group), an aryloxy group (e.g., a phenoxy, p-chlorophenoxy, p-nitrophenoxy, naphthoxy, etc. group), an alkoxy group (e.g., a methoxy, etc. group), a halogen atom (e.g., a chlorine, fluorine, etc. atom), an arylazo group (e.g., a phenylazo, naphthylazo, etc. group), an aryltriazolyl group (e.g., a 1-benzotriazolyl, 2-benzotriazolyl, 2-naphthotriazolyl, etc. group), an alkylthio group (e.g., an alkylthio group having 4 to 10 carbon atoms, etc.), an arylthio group (e.g., a phenylthio, naphthylthio, etc. group), a heterocyclic thio group (e.g., a 2-benzothiazolylthio, 1-phenyl-5-tetrazolylthio, 2-benzoxazolylthio, 2-benzimidazolylthio, 5-phenyl-1,3,4-oxadiazolyl-2-thio, etc. group), a cycloalkylthio group (e.g., a cyclohexylthio, etc. group), a cycloalkoxy group (e.g., a cyclohexyloxy, etc. group), an imido group (e.g., a phthalimido, succinimido, 5,5- dimethyl-3-oxazolidinyl, etc. group), an imidazolyl group (e.g., a 1-imidazolyl, 2-methyl-1-imidazolyl, 1-benzimidazolyl, etc. group), a triazolyl group (e.g., a 3,5-diethyl-1,2,4-triazolyl, etc. group), an acylamino group (e.g., a benzamido, acetylamino, etc. group), a sulfonamido group (e.g., a benzenesulfonamido, methanesulfonamido, etc. group), a cycloamino group (e.g., a piperidino, morpholino, etc. group).

In the general formula (I), suitable halogen atoms represented by X and Y and as substituents on R and Z are, for example, a fluorine atom, a chlorine atom and a bromine atom.

The magenta color forming couplers represented by the general formula (I) above are novel couplers.

Of these magenta color forming couplers employed in the present invention, particularly preferred couplers are those represented by the general formula (II) below.

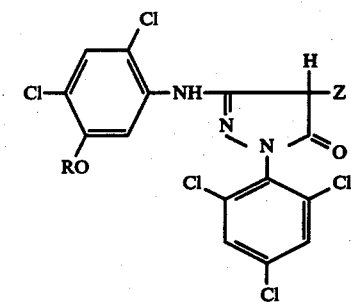

(II)

wherein R and Z have the same meanings as defined in the general formula (I). The coupler represented by the general formula (II) is particularly preferred because the spectral absorption curve of the magenta color images obtained especially upon color development is sharp, a second absorption zone which is characteristic of conventional pyrazolone type magenta couplers is small, and the melting point thereof is low and, further, solubility in an organic solvent having a high boiling point is high.

3-Anilino-5-pyrazolone type couplers having an alkoxy group at the ortho position of the anilino group are mentioned in U.S. Pat. No. 3,935,015 and British Patent No. 956,261. While it is very clear that the coupler represented by the general formula (II) has a unique structure since chlorine atoms are present at the ortho and para positions and an alkoxy group, an aryloxy group or a heterocyclic oxy group is present at the 5-position of the anilino group, the coupler represented by the general formula (II) has, when compared with the 3-(2-alkoxy)anilino-5-pyrazolone type couplers described in U.S. Pat. No. 3,935,015 and British Patent No. 956,261, excellent color fastness of the magenta color images obtained, particularly when color developed, i.e., fading on irradiation with light is minimal, and yellow staining at the unexposed areas of the color photographic light-sensitive element after color development processing is low and, further, the degree that this yellow staining is increased upon irradiation with light is minimal.

Furthermore, the 3-(2-alkoxy)anilino-5-pyrazolone type couplers have a fatal defect in color reproduction in that the absorption wavelength of the magenta color images obtained upon color development was inclined toward an overly short wavelength side.

Specific examples of magenta color forming couplers which can be employed in the present invention are shown below, but the present invention is not to be construed as being limited thereto.

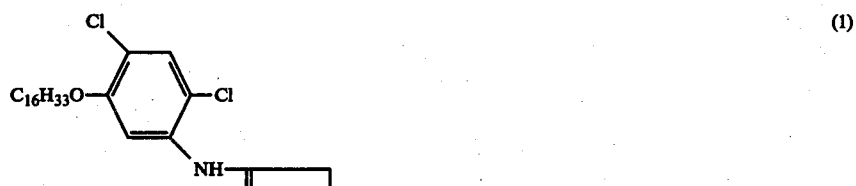

(1)

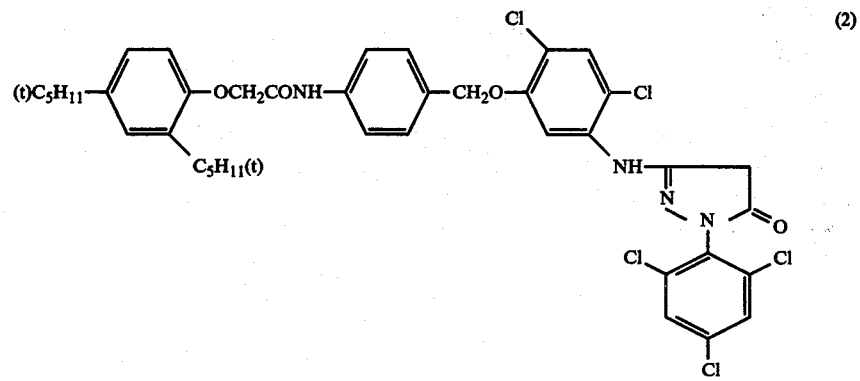

(2)

-continued
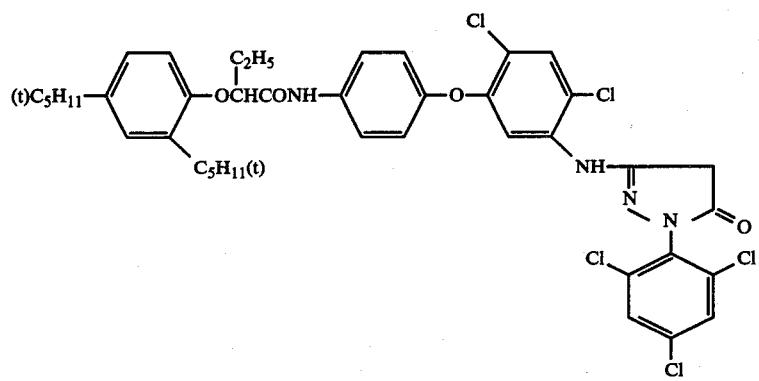 (3)
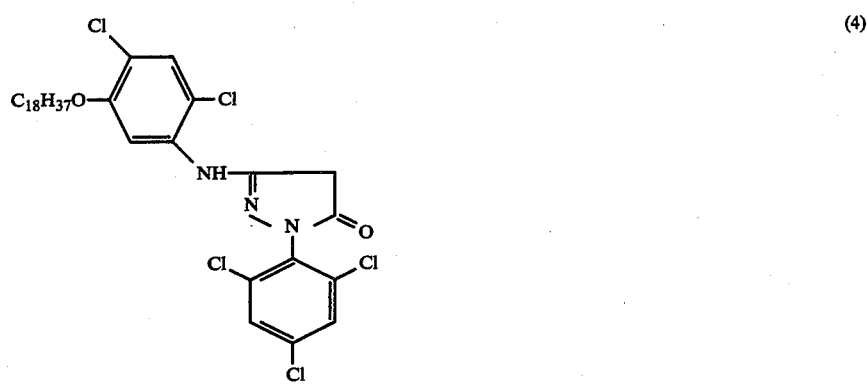 (4)
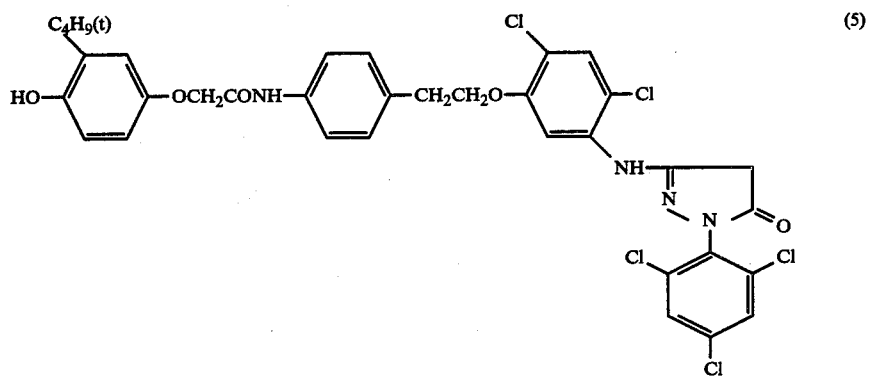 (5)
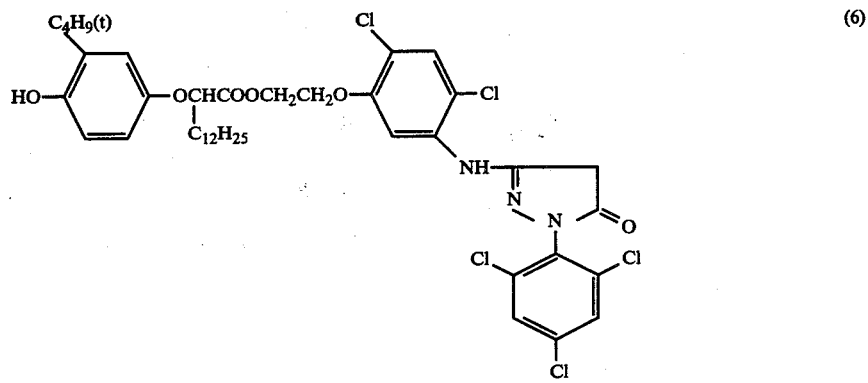 (6)

-continued
(7)
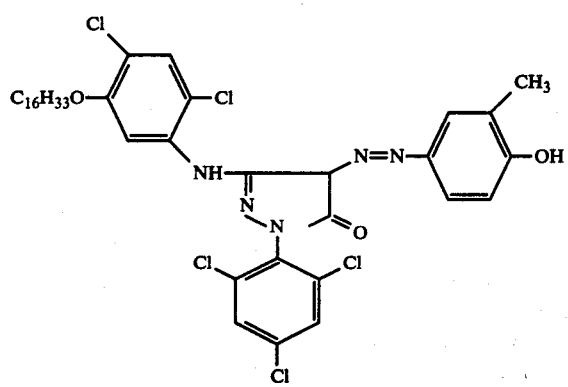
(8)
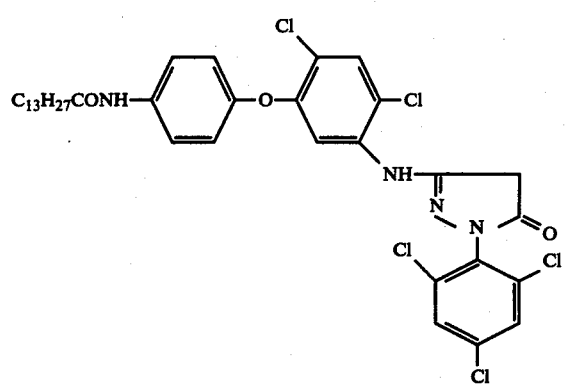
(9)
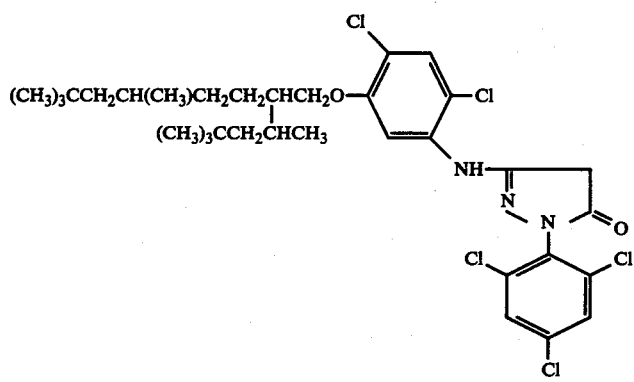
(10)
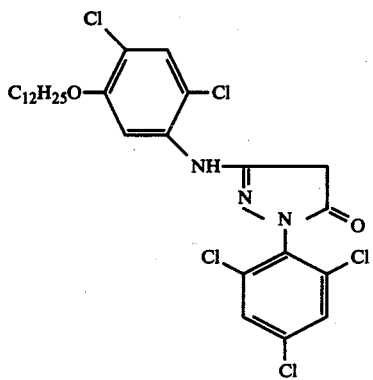

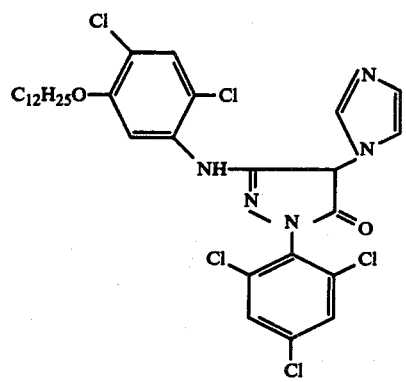
(11)
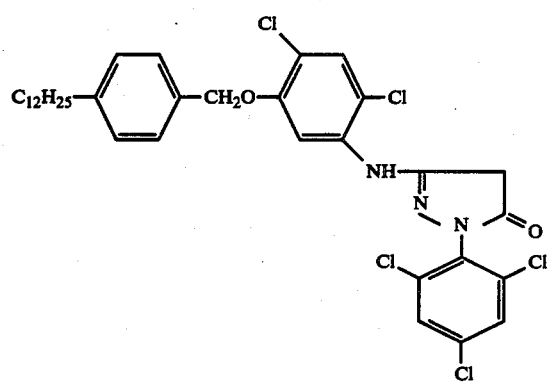
(12)
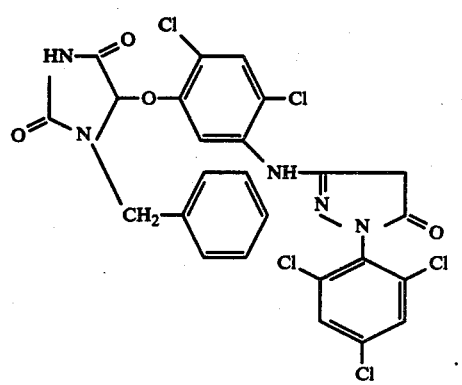
(13)
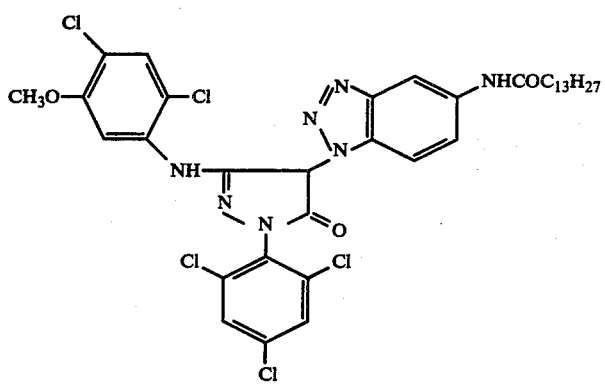
(14)

-continued
(15)
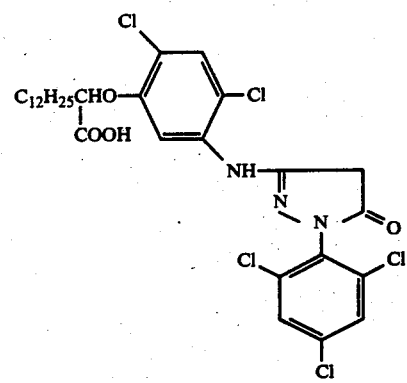
(16)
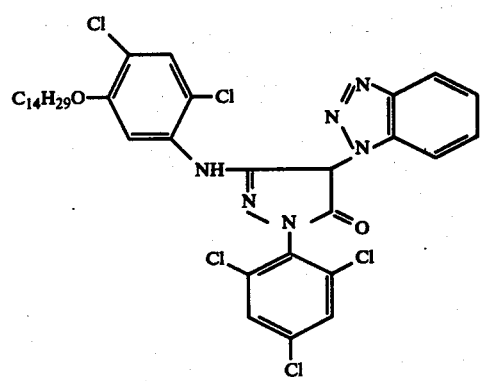
(17)
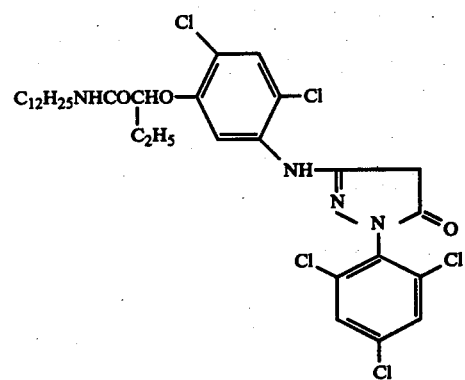
(18)
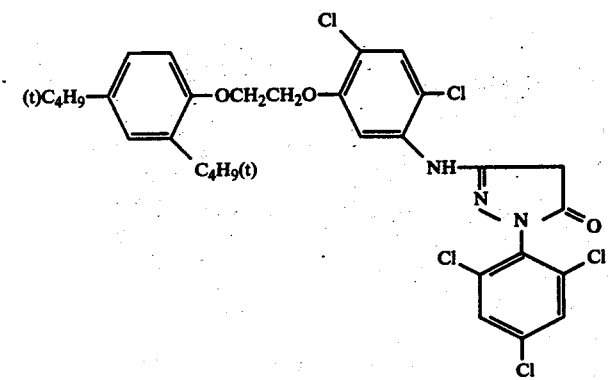

(19)
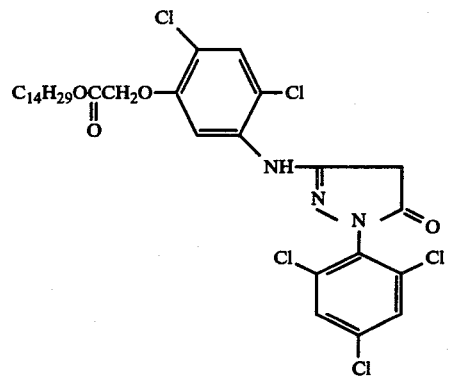
(20)
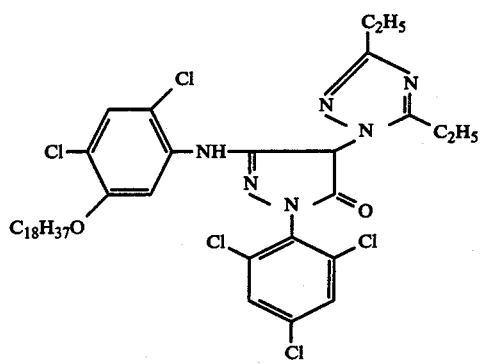
(21)
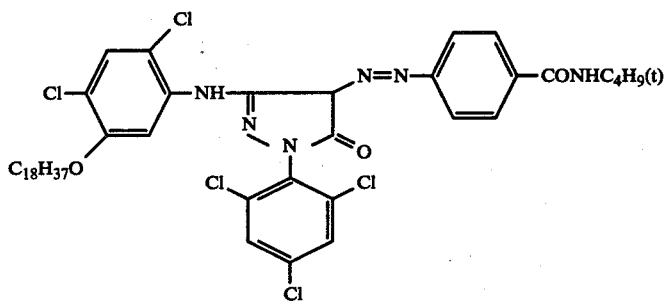
(22)
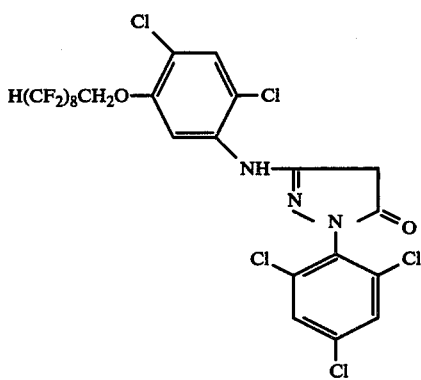
The magenta color forming couplers of the general formula (I) of the present invention can be synthesized as follows.
Step (A)
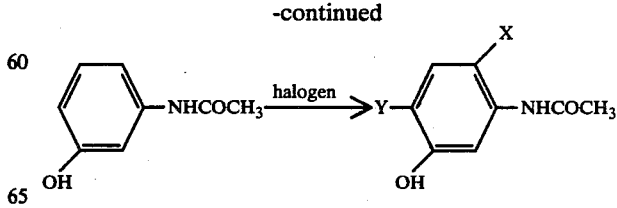
3-Acetaminophenol is reacted with a halogen in a solvent such as acetic acid and a chlorinated solvent preferably at about 0° to about 25° C. to form a 4,6-dihalo-3-acetaminophenol. A suitable molar proportion of halogen to 3-acetaminophenol is 2:1 when X and Y are the same and 1:1 when X and Y are different.

Step (B)

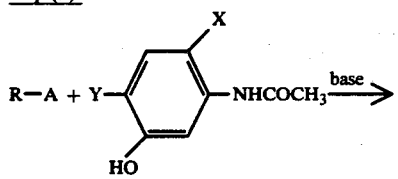

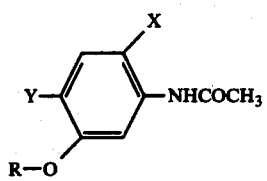

The 4,6-dihalo-3-acetaminophenol obtained as described above is reacted with a halide compound represented by the formula R-A wherein A is a halogen atom and R is the same as defined above in a solvent such as an alcohol, e.g., ethanol, isopropanol, etc., dimethylformamide, dimethyl sulfoxide, a chlorinated solvent, toluene, xylene, etc., in the presence of a base such as potassium hydroxide, sodium hydroxide, triethylamine, etc., preferably at about 40° to about 150° C. to form an O-substituted-4,6-dihalo-3-acetaminophenol.

Step (C)

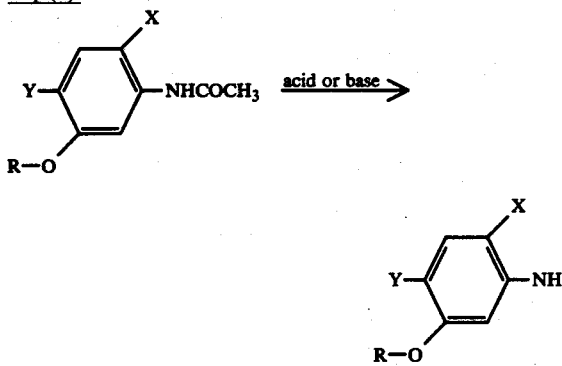

Then, the O-substituted-4,6-dihalo-3-acetaminophenol prepared as described above is hydrolyzed with an acid, such as hydrochloric acid, etc., or a base, such as sodium hydroxide, potassium hydroxide, etc., in an aqueous alcohol solution preferably at about 50° to about 120° C. to form a 2,4-dihalo-5-substituted aniline.

Step (D)

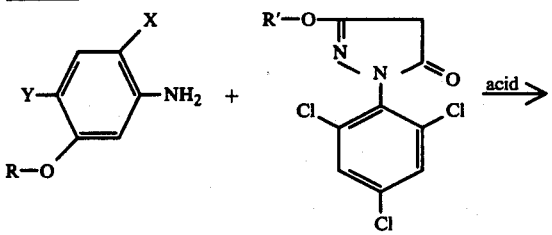

-continued

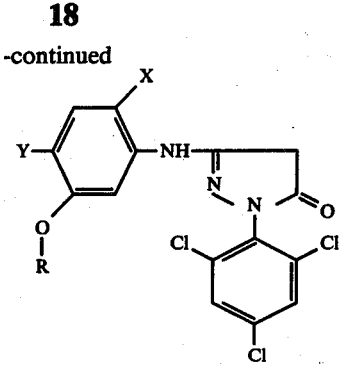

The 2,4-dihalo-5-substituted aniline produced as described above is reacted with 1-(2,4,6-trichlorophenyl)-3-alkoxy-2-pyrazolin-5-one in the presence of an acid catalyst such as hydrochloric acid, acetic acid, sulfuric acid, p-toluenesulfonic acid, methanesulfonic acid, etc., in the absence of a solvent. Suitable examples of the alkoxy substituents include a methoxy group, an ethoxy group, a propoxy group, etc.

The above procedure is described in U.S. Pat. No. 3,615,506.

Typical synthesis examples of representative compounds of the general formula (I) are illustrated hereinbelow. Unless otherwise indicated herein, all parts, percents, ratios and the like are by weight.

SYNTHESIS EXAMPLE 1

Synthesis of 1-(2,4,6-Trichlorophenyl)-3-(2,4,-dichloro-5-hexadecyloxyanilino)-2-pyrazolin-5-one (Coupler (1))

(1) Synthesis of N-Acetyl-2,4-dichloro-5-hexadecylaniline

In a solution of 5.6 g of potassium hydroxide in 200 ml of ethanol was dissolved 22 g of 4,6-dichloro-3-acetaminophenol (which was synthesized using the method described in Beilstein, 13, I, 135). To the solution was added 30.5 g of hexadecyl bromide. After the mixture was stirred for an hour at room temperature (about 20-30° C.), the mixture was heated at reflux for 8 hours. The reaction mixture was poured into water. The resulting precipitate was recovered by filtration and washed with methanol to obtain 32 g of the desired product. The melting point thereof was 92 to 93.5° C.

(2) Synthesis of 2,4-Dichloro-5-hexadecyloxyaniline

N-Acetyl-2,4-dichloro-5-hexadecyloxyaniline obtained in Step (1) above, 20 g, was heated at reflux with stirring, in a solvent mixture of 150 ml of ethanol and 60 ml of hydrochloric acid, for 5 hours. Then, the reaction mixture was allowed to stand. The crystals precipitated were recovered by filtration to obtain 16 g of hydrochloride of the desired product.

(3) Synthesis of 1-(2,4,6-Trichlorophenyl)-3-(2,4-dichloro-5-hexadecyloxyanilino)-2-pyrazolin-5-one A mixture of 16 g of the 2,4-dichloro-5-hexadecyloxyaniline hydrochloride obtained in Step (2) described above and 12 g of 1-(2,4,6-trichlorophenyl)-3-ethoxy-2-pyrazolin-5-one was heated to 150° C. and melted. Thereafter, the mixture was reacted at 150 to 160° C. for an hour under a reduced pressure (approximately 20 mm Hg) with stirring while removing the ethanol formed. The reaction mixture was allowed to cool to 100° C. and then 100 ml of ethanol was added thereto. After heating with stirring, the mixture was allowed to cool to room temperature. The precipitate was recovered by filtration. After drying, the precipitate was recrystallized from 100 ml of ethyl acetate to obtain 16 g of the desired coupler. The melting point thereof was 107 to 108° C.

Elemental Analysis ($C_{31}H_{40}N_3Cl_5O_2$)
Calcd. (%): C 56.08 H 6.07 N 6.33
Found (%): C 56.29 H 6.09 N 6.48

SYNTHESIS EXAMPLE 2

Synthesis of 1-(2,4,6-Trichlorophenyl)-3-(2,4-dichloro-5-octadecyloxyanilino)-2-pyrazolin-5-one (Coupler (4))

Using 18 g of 2,4-dichloro-5-octadecyloxyaniline hydrochloride and 13 g of 1-(2,4,6-trichlorophenyl)-3-ethoxy-2-pyrazolin-5-one, which were prepared in a manner similar to Steps (1) and (2) of Synthesis Example 1, similar procedures to Step (3) of Synthesis Example 1, were carried out and recrystallization was performed from 100 ml of ethanol to obtain 15 g of the desired coupler. The melting point thereof was 98 to 99° C.

Elemental Analysis ($C_{33}H_{44}N_3Cl_5O_2$)
Calcd. (%): C 57.27 H 6.41 N 6.07
Found (%): C 57.16 H 6.37 N 6.11

SYNTHESIS EXAMPLE 3

Synthesis of 1-(2,4,6-Trichlorophenyl)-3-[2,4-dichloro-5-(4-tetradecanoylaminophenoxy)anilino]-2-pyrazolin-5-one (Coupler (8))

(1) Synthesis of 1-(2,4,6-Trichlorophenyl)-3-[2,4-dichloro-5-(4-nitrophenoxy)anilino]-2-pyrazolin-5-one Using 11.6 g of 2,4-dichloro-5-(4-nitrophenoxy)-aniline hydrochloride and 13.1 g of 1-(2,4,6-trichlorophenyl)-3-ethoxy-2-pyrazolin-5-one, which were prepared in a manner similar to Steps (1) and (2) of Synthesis Example 1 except that 21.2 g of 4-fluoronitrobenzene was used in lieu of hexadecyl bromide in Step (1) of Synthesis Example 1, procedures similar to Step (3) of Synthesis Example 1 were carried out. In this case, 10.0 g of the desired product was obtained without recrystallization. The melting point thereof was 305 to 306° C.

(2) Synthesis of 1-(2,4,6-Trichlorophenyl)-3-[2,4-dichloro-5-(4-aminophenoxy)anilino]-2-pyrazolin-5-one In a solvent mixture of 100 ml of glacial acetic acid, 10 ml of methanol and 10 ml of water was dispersed 10 g of 1-(2,4,6-trichlorophenyl)-3-[2,4-dichloro-5-(4-nitrophenoxy)anilino]-2-pyrazolin-5-one prepared as described in Step (1) above. To the dispersion was added 10 g of iron powder with heating under stirring over a 10 minute period. The reaction mixture was poured into 1 l of water and the precipitate crystallized out was recovered by filtration to obtain 8 g of the desired compound.

(3) Synthesis of 1-(2,4,6-Trichlorophenyl)-3-[2,4-dichloro-5-(4-tetradecanoylaminophenoxy)anilino]-2-pyrazolin-5-one In a solvent mixture of 80 ml of acetic acid and 100 ml of acetonitrile were dispersed 8 g of 1-(2,4,6-trichlorophenyl)-2-[2,4-dichloro-5-(4-aminophenoxy)anilino]-2-pyrazolin-5-one obtained in accordance with Step (2) above and 1.5 g of anhydrous sodium acetate. To the dispersion was dropwise added 3.9 g of myristic acid chloride over a 10 minute period at room temperature while stirring the mixture. After stirring the mixture for an hour at room temperature, the reaction mixture was poured into 500 ml of water, followed by extraction with 300 ml of ethyl acetate. The ethyl acetate solution layer was separated. After thoroughly washing the ethyl acetate solution obtained with water, the system was dried over anhydrous sodium sulfate. Ethyl acetate was distilled off under reduced pressure. The residue was recrystallized from a solvent mixture of acetonitrile and ethyl acetate (10:1 by volume) to obtain 9.7 g of the desired coupler. The melting point thereof was 111 to 114° C.

Elemental Analysis ($C_{35}H_{39}N_4Cl_5O_3$) Calcd. (%): C 56.73 H 5.31 N 7.56 Found (%): C 56.62 H 5.32 N 7.82

The magenta color forming coupler in accordance with the present invention possesses both high coupling activity and sufficient solubility in an organic solvent, and, therefore, a color photographic element prepared using this coupler provides photographic properties such as a good sensitivity, gradation and the like, and possesses the characteristic that the coupler is easy to prepare. Moreover, the color photographic element has the characteristics that not only does the photographic color image obtained by the development processing thereof possess a spectral absorption characteristic which is effective for color reproduction and sufficient light fastness, but also, after color development processing, yellow stain is reduced at the unexposed portions and an increase in the yellow stain is minimal even on exposure to light for a long period of time, and, further, fading of the photographic color images due to light is markedly reduced.

Furthermore, the magenta color image obtained from the coupler in accordance with the present invention is resistant to actions due to heat and humidity. That is, the degree of color fading due to heat is serious with color images fromed from 5-pyrazolones having an acylamino group or a ureido group at the 3-position thereof as described in U.S. Pat. No. 2,600,788. This is believed to be due to the fact that the dyes formed would react with the remaining coupler to produce a colorless product. For preventing color fading, a processing using a stabilizing solution containing formaldehyde or the like has been practiced, in general. A characteristic of the coupler of the present invention is that a sufficient fastness without necessitating any such processing is obtained.

In order to prepare a silver halide photographic light-sensitive element using the coupler of the present invention, one kind of coupler of the present invention can be used individually, or two kinds thereof can be used as a mixture thereof, or the coupler can also be used in combination with magenta color image forming couplers other than the coupler of the present invention. Further, in order to enhance the color reproduction of color photographic lightsensitive elements, the magenta coupler of the present invention can also be used in the same emulsion layer in combination with a cyan or yellow coupler which has a different hue. Generally, a suitable molar proportion of the magenta color coupler of the present invention to the silver halide present is about 1:2 to about 1:60, preferably 1:2 to 1:10.

The photographic emulsion containing the coupler of the present invention can be coated onto conventional photographic supports such as synthetic resins, baryta papers, resin coated papers or the like, and a variety of color light-sensitive elements such as a color positive film, a color negative film, a color reversal film, a color printing paper, etc., can thus be prepared. A suitable silver coating amount is about 20 to about 400 mg/cm², preferably 40 to 200 mg/cm².

Silver halides, such as silver chloride, silver bromide, silver iodide, silver chlorobromide, silver chloroiodide, silver chlorobromoiodide or the like are used in the photographic emulsion used in the color photographic light-sensitive element of the present invention. These photographic emulsions can, if desired, contain natural sensitizing agents which are present in gelatin, sulfur sensitizing agents, noble metal salts as well as reducing sensitizing agents. Further, optical sensitizing agents can also be incorporated in the photographic emulsion in order to impart an appropriate color sensitivity thereto. Conventional photographic additives, such as an anti-foggant, a stabilizer, an irradiation preventing dye, a coating aid, a plasticizer, a hardening agent and the like can optionally be incorporated therein.

p-Substituted phenol derivatives are advantageously present in the color photographic light-sensitive element in accordance with the present invention, together with the coupler of the present invention. Specific examples of p-substituted phenol derivatives which are particularly suitable for the color photographic light-sensitive element of the present invention include hydroquinone derivatives as described in U.S. Pat. Nos. 2,360,290, 2,418, 613, 2,675,314, 2,701,197, 2,704,713, 2,728,659, 2,732,300, 2,735,765, 2,710,801 and 2,816,028; gallic acid derivatives as described in U.S. Pat. Nos. 3,457,079 and 3,069,262, and Japanese Patent Publication No. 13496/68; p-alkoxyphenols as described in U.S. Pat. No 2,735,765 and Japanese Patent Application (OPI) No. 4738/72; p-oxyphenol derivatives as described in U.S. Pat. Nos. 3,432,300, 3,573,050 and 3,574,627, as well as Japanese Patent Publication No. 20977/74; and the like.

The hydrophilic colloid layers containing the coupler of the present invention, particularly a gelatin layer, can be hardened using a variety of cross-linking agents. In most cases, for example, inorganic compounds, such as a chromium salt or a zirconium salt, mucochloric acid or aldehyde type cross-linking agents, such as 2-phenoxy-3-chloromaleic aldehyde as described in Japanese Patent Publication No. 7133/69 can be advantageously employed in the present invention. Non-aldehyde type cross-linking agents such a polyepoxy compounds described in Japanese Patent Publication No. 7133/69, poly-(1-aziridinylated) compounds as described in Japanese Patent Publication No. 8790/62, as well as active halogen compounds as described in U.S. Pat. Nos. 3,362,827 and 3,325,287 are particularly useful for the practice of the present invention.

The color photographic light-sensitive element containing the coupler of the present invention can be processed using conventional processing methods. That is, after image-wise exposure to light, the color photographic light-sensitive element is developed with a developer containing a p-phenylenediamine type developing agent and thereafter bleached and fixed. Thus, a color image having excellent spectral absorption characteristics and transparency is formed.

Typical examples of developing agents which are suitable for development of the color light-sensitive element in accordance with the present invention include 4-(N,N-diethylamino)aniline, 4-(N-ethyl-N-$\beta$-methanesulfonamidoethyl)-amino-2-methylaniline, 4-(N-ethyl-N-$\beta$-hydroxyethyl)amino-2-methylaniline, 4-N,N-diethylamino-2-methylaniline, etc.

Good results can be obtained with the color photographic light-sensitive element containing the coupler of the present invention by applying color development processing thereto, for example, a method which comprises halogenationbleaching the developed silver formed by color development as described in U.S. Pat. Nos. 2,439,901, 2,623,822, 2,814,565, 3,372,028 and the like, and color developing again to thereby increase the amount of a dye formed, or a method which comprises decreasing the amount of silver halide in the light-sensitive element using a color intensifying method as described in U.S. Pat. 3,674,490, Japanese Patent Application (OPI) No. 9728/73, Japanese Patent Application No. 128327/74 or the like.

The photographic light-sensitive element which is employed in the present invention can also contain, as desired, an intermediate layer, an antihalation layer, a protective layer, a yellow filter layer, a backing layer, a mordant polymer layer, a developer-stain preventing layer and the like coated onto a support (including the back surface thereof) in addition to the silver halide emulsion layers. Silver halide emulsion layers for color photography include a red sensitive silver halide emulsion layer, a green sensitive silver halide emulsion layer and a blue sensitive silver halide emulsion layer. The order of these layers is not limited and each of the respective layers can be divided into two or more layers for use.

The characteristics obtained in employing the magenta coupler of the present invention are more specifically explained below by reference to some specific examples. For comparison, the magenta couplers indicated below, which are structurally similar to the magenta coupler of the present invention, were used.

Comparison Coupler (A)

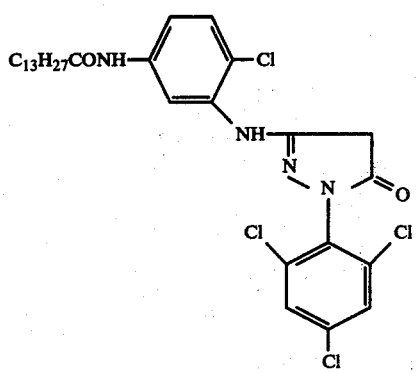

Comparison Coupler (B)

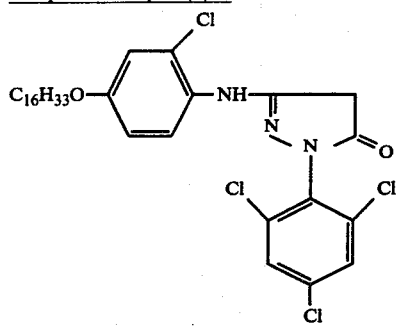

Comparison Coupler (C)

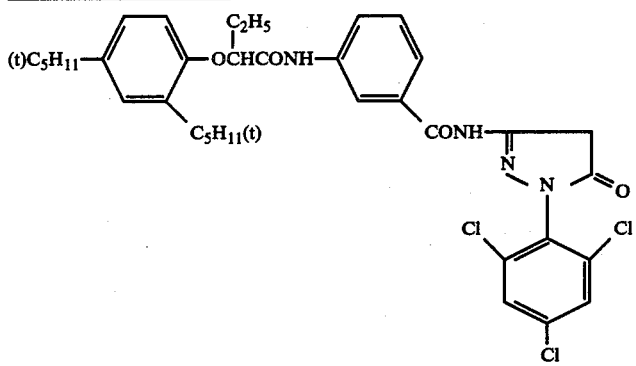

Comparison Coupler (D)

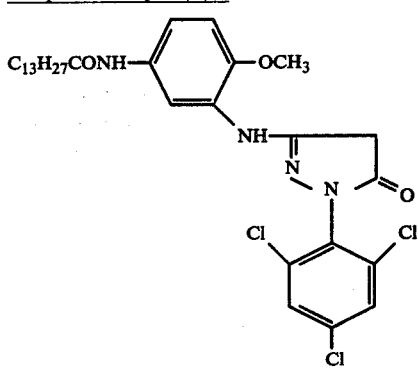

Comparison Coupler (E)

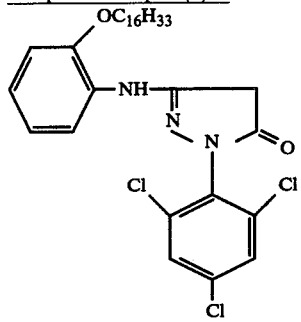

With Comparison Couplers (A), (B), (D) and (E) indicated above and with Couplers (4) and (8) of the present invention, the spectral absorption characteristics of an azomethine dye formed by the oxidation coupling reaction with 4-[N-ethyl-N-(β-methanesulfonamidoethyl)]amino-2-methylaniline were measured in ethyl acetate and compared.

From the spectral absorption curves obtained, the color density of the main wavelength was adjusted to 1.00 and the density of a second absorption appearing in the blue light region, the density at a longer wavelength said by 60 mμ from the main wavelength and the width of the wavelength at which the color density became 0.50 were determined. The results obtained are shown in Table 1 below.

Table 1

|  | Color Density of Second Absorption | Color Density at 60 mµ Longer Wavelength Side | Width of Wavelength Having Density of 0.5 | Peak of Main Wavelength (mµ) |
|---|---|---|---|---|
| Coupler (4) | 0.125 | 0.128 | 66 | 532 |
| Coupler (8) | 0.126 | 0.125 | 65 | 532 |
| Comparison Coupler (A) | 0.141 | 0.134 | 67 | 529 |
| Comparison Coupler (B) | 0.159 | 0.165 | 74 | 524 |
| Comparison Coupler (D) | 0.164 | 0.152 | 72 | 521 |
| Comparison Coupler (E) | 0.173 | 0.159 | 75 | 518 |

The color image obtained using the coupler of the present invention is sharply cut off at the long wavelength side and the undesired second absorption is minimal. Further, the position of the main wavelength is appropriate, which are preferred in color reproduction. This is believed to be because the coupler of the present invention possesses chlorine atoms at the 2- and 4-positions of and an ether bond at the 5-position of the anilino ring thereof.

The characteristics obtained using the magenta coupler of the present invention are explained by reference to the examples hereinbelow.

EXAMPLE 1

A solution obtained by dissolving 4 g of Coupler (1) of the present invention, 4.0 ml of tricresyl phosphate and 12 ml of ethyl acetate with heating at 60° C. was added to 40 ml of an aqueous solution containing 0.10 g of sodium dodecylbenzenesulfonate of 60° C. The solution mixture was stirred with a homogenizer to prepare a coupler dispersion. The coupler dispersion was mixed with 100 g of a red sensitive photographic emulsion containing $4.70 \times 10^{-2}$ mol of silver chlorobromide (50 mol% silver chloride) and 9 g of gelatin, and 5 ml of a 3% acetone solution of triethylenephosphoramide was further added thereto as a hardening agent. After adjusting the pH to 7.0, the dispersion was coated onto a paper sheet having coated thereon polyethylene in a thickness of 3.4 microns (dry thickness; hereafter all thicknesses given are as a dry thickness). Gelatin was coated thereon (using a 2% gelatin aqueous solution) in a thickness of 1 micron to prepare a color print paper (Sample (H)).

Color print papers were prepared in a manner similar to the preparation of Sample (H) except that Couplers (4) and (8) were employed in lieu of Coupler (1) and Couplers (A), (B), (D) and (E) were employed as magenta color image forming couplers for comparison, respectively. Samples (I) and (J) were prepared from Couplers (4) and (8), and Samples (K), (L), (M) and (N) were prepared from Comparison Couplers (A), (B), (D) and (E), respectively.

These samples were exposed to green light (500 CMS, color temperature of 2854° K.) for 1 second using a step wedge and processed with the following development processings.

| Processing Step | Temp. | Time |
|---|---|---|
| 1. Color Development | 30° C | 4 min |
| 2. Bleach Fixing | " | 2 min |
| 3. Water Washing | " | 2 min |
| 4. Stabilizing | " | 2 min |

| Composition of Color Developer | | |
|---|---|---|
| Sodium Metaborate | 25 | g |
| Sodium Sulfite | 2 | g |
| Hydroxylamine (sulfate) | 2 | g |
| Potassium Bromide | 0.5 | g |
| 6-Nitrobenzimidazole (nitrate) | 0.02 | g |
| Sodium Hydroxide | 4 | g |
| Benzyl Alcohol | 15.8 | ml |
| Diethylene Glycol | 20 | ml |
| 4-(N-Ethyl-N-β-methanesulfonamidoethyl)-amino-2-methylaniline Sesquisulfate | 8 | g |
| Water to make | 1 | l |
| Composition of Bleach Fixing Solution | | |
| Ferric Salt of Ethylenediamine-Tetraacetate | 45 | g |
| Ammonium Thiocyanate | 10 | g |
| Sodium Sulfite | 10 | g |
| Ammonium Thiosulfate (60% aq. soln.) | 100 | ml |
| Tetrasodium Ethylenediamine Tetraacetate | 5 | g |
| Water to make | 1 | l |
| Composition of Stabilizing Bath (a) | | |
| Tartaric Acid | 10 | g |
| Zinc Sulfate | 10 | g |
| Sodium Metaborate | 20 | g |
| Water to make | 1 | l |

With respect to the samples obtained, the yellow stain density at the unexposed area was determined by measuring the reflection density thereof with a densitometer equipped with a blue filter, respectively. Thereafter, these samples were stored for 2 weeks under a fluorescent light (about 28,000 lux) and the increased rate in the yellow stain density was measured. The results obtained are shown in Table 2 below.

Table 2

| Sample No. | Coupler Used | Yellow Stain Density at Unexposed Area | |
|---|---|---|---|
| | | Initial Density | After Irradiation |
| (H) | Coupler (1) | 0.01 | 0.08 |
| (I) | Coupler (4) | 0.01 | 0.09 |
| (J) | Coupler (8) | ≦0.01 | 0.06 |
| (K) | Comparison Coupler (A) | 0.02 | 0.12 |
| (L) | Comparison Coupler (B) | 0.02 | 0.14 |
| (M) | Comparison Coupler (D) | 0.04 | 0.20 |
| (N) | Comparison Coupler (E) | 0.03 | 0.13 |

It is clear from the results shown in Table 2 above that the samples using the magenta couplers of the present invention provide a reduced yellow stain density at the unexposed areas and less increase in yellow stain density upon irradiation with light.

EXAMPLE 2

Onto a paper sheet whose surface was covered with polyethylene were coated, as a first layer, a blue sensitive photographic emulsion containing silver chlorobromide (20 mol% chloride) containing α-pivaloyl-α-(5,5-dimethyl-3-hydantoinyl)-2-chloro-5-[α-(2,4-di-tert-amylphenoxy)butyramido]acetanilide in a thickness of 3.0 microns (silver coating amount: 300 mg/m²), and thereon gelatin in a thickness of 1.5 microns as a second layer in a manner similar to Example 1.

A solution obtained by dissolving 4 g of Coupler (1) of the present invention, 0.3 g of 2,5-di-tert-octylhydroquinone, 0.4 g of 6,6'-dihydroxy-7,7'-dimethoxy-4,4,4',4'-tetramethylbis-2,2'-spirochroman, 4.0 ml of tricresyl phosphate and 12 ml of ethyl acetate with heating at 60° C. was added to 40 ml of an aqueous solution containing 4 g of gelatin and 0.10 g of sodium dodecylbenzenesulfonate at 60° C. The solution mixture was stirred with a homogenizer to prepare a coupler dispersion. The coupler dispersion was mixed with 100 g of a green sensitive photographic emulsion containing 4.70 × 10⁻² mol of silver chlorobromide (50 mol% silver chloride) and 9 g of gelatin and 5 ml of a 3% acetone solution of triethylene phosphoramide was added thereto as a hardening agent. After adjusting the pH to 7.0, the dispersion was coated on the above-described second layer as a third layer in a thickness of 3.4 microns. Then, gelatin containing 2-(5-chlorobenzotriazol-2-yl)-4-methyl-6-tert-butylphenol and 2-benzotriazol-2-yl)-4-tert-butylphenol was coated in a thickness of 1.5 microns as a fourth layer. A red sensitive photographic silver chlorobromide emulsion (50 mol% silver chloride) containing 2-[α-(2,4-di-tert-amylphenoxy)butyramido]-4,6-dichloro-5-methylphenol in a thickness of 2.5 microns (silver coating amount: 300 mg/m²) as a fifth layer, and finally as an uppermost layer, gelatin was coated in a thickness of 1 micron to prepare a color printing paper (Sample (O)).

Color printing papers were prepared in a manner similar to Sample (O) except that, in lieu of Coupler (1), Magenta Couplers (4) and (8) were further employed, as magenta color image forming couplers, and Comparison Couplers (A), (B), (C), (D) and (E) were employed.

The samples obtained from Couplers (4) and (8) of the present invention are designated Samples (P) and (Q), and Samples (R), (S), (T), (U) and (V) from Comparison Couplers (A), (B), (C), (D) and (E), respectively.

These samples were exposed to a green light (500 CMS, color temperature of 2854° K.) for 1 second using a step wedge and development processings similar to Example 1 were performed. With respect to Samples (O), (Q) and (T), development processing in which a Stabilizing Bath (b) containing formaldehyde was employed in lieu of Stabilizing Bath (a) shown in Example 1 was also performed.

| Composition of Stabilizing Bath (b) | |
|---|---|
| Tartaric Acid | 10 g |
| Zinc Sulfate | 10 g |
| Sodium Metaborate | 20 g |
| Formaldehyde (40% aq. soln.) | 10 ml |
| Water to make | 1 l |

Each of the respective samples was subjected to the development processing described above. The thus-formed color images were stored for two weeks under a fluorescent light (about 28,000 lux) and the rate (%) of decrease in color density was measured at an initial density of 1.0 of the magenta color images. The results obtained are shown in Table 3 below.

Table 3

| | Light Fastness of Color Image | | |
|---|---|---|---|
| Sample No. | Coupler Employed | Stabilizing Bath | Rate of Decrease in Color Density (%) |
| (O) | Coupler (1) | (a) | 11 |
| (P) | Coupler (4) | (a) | 10 |
| (Q) | Coupler (8) | (a) | 8 |
| (R) | Comparison Coupler (A) | (a) | 22 |
| (S) | Comparison Coupler (B) | (a) | 45 |
| (T) | Comparison Coupler (C) | (a) | 35 |
| (U) | Comparison Coupler (D) | (a) | 42 |
| (V) | Comparison Coupler (E) | (a) | 28 |

Then, of these, Samples (O), (Q) and (T) were stored at 120° C. for 4 hours, and at 60° C. under 75% RH for three weeks, and the rate of decrease in color density to an initial color density of the magenta color images was measured. The results obtained are shown in Table 4 below.

Table 4

| | | | Fastness of Color Image to Heat and Humidity | | | |
|---|---|---|---|---|---|---|
| | | | 120° C 4 Hours | | 60° C 75% RH 3 Weeks | |
| | | | Initial Density | | Initial Density | |
| Sample No. | Coupler Employed | Stabilizing Bath | 0.5 | 1.0 | 0.5 | 1.0 |
| (O) | Coupler (1) | (a) | 6 | 4 | 10 | 9 |
| | | (b) | 6 | 4 | 9 | 9 |
| (Q) | Coupler (8) | (a) | 7 | 5 | 10 | 8 |
| | | (b) | 6 | 4 | 9 | 6 |
| (T) | Comparison Coupler (C) | (a) | 42 | 37 | 65 | 37 |
| | | (b) | 16 | 10 | 21 | 13 |

It can be seen that the couplers of the present invention provide color images which are extremely fast to light, and also form color images which are sufficiently fast to heat and humidity without necessitating the use of a stabilizing bath containing formaldehyde.

Further, these samples were exposed to light through a transparent original having a color negative image thereon, and development processings were performed as above indicated to thereby obtain color prints. The red portion of the print obtained from Sample (O) in accordance with the present invention was less dark and was sharper in comparison with that of Sample (T) and of Sample (U) containing the comparison couplers indicated above.

While the invention has been described in detail and with reference to specific embodiments thereof, it will be apparent to one skilled in the art that various changes and modifications can be made therein without departing from the spirit and scope thereof.

What is claimed is:

1. A color photographic light-sensitive element comprising a support having thereon a silver halide emulsion layer containing therein a 3-anilino-2-pyrazolin-5-one magenta color forming coupler represented by the general formula (II):

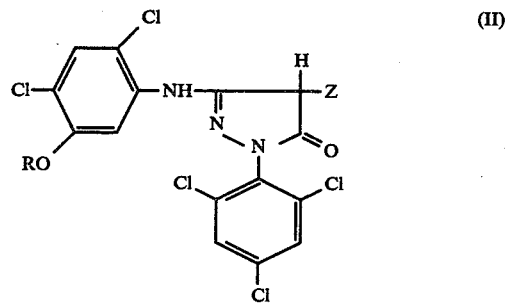

wherein R represents an alkyl group and Z represents a hydrogen atom.

2. The color photographic light-sensitive element of claim 1, wherein said silver halide emulsion layer is a green sensitive silver halide emulsion layer.

3. The color photographic light-sensitive element of claim 1, wherein said silver halide emulsion layer is a green sensitive silver halide emulsion layer containing said magenta color forming coupler represented by the general formula (I) and said color photographic light-sensitive element additionally includes a red sensitive silver halide emulsion layer containing a phenolic or naphtholic cyan color forming coupler, and a blue sensitive silver halide emulsion layer containing an acylacetamido yellow color forming coupler.

4. The color photographic light-sensitive element of claim 1, wherein said silver halide emulsion layer contains a p-oxyphenol derivative or a hydroquinone compound.

* * * * *